(12) United States Patent
Smith et al.

(10) Patent No.: US 8,433,723 B2
(45) Date of Patent: Apr. 30, 2013

(54) SYSTEMS, METHODS, AND APPARATUS FOR PROCESSING DOCUMENTS TO IDENTIFY STRUCTURES

(75) Inventors: Robin Y. Smith, San Jose, CA (US);
William B. Ballard, Raleigh, NC (US);
Scott G. Flicker, Raleigh, NC (US);
Sean G. Greenhow, Raleigh, NC (US)

(73) Assignee: Cambridgesoft Corporation, Cambridge, MA (US)

( * ) Notice: Subject to any disclaimer, the term of this patent is extended or adjusted under 35 U.S.C. 154(b) by 58 days.

(21) Appl. No.: 13/100,217

(22) Filed: May 3, 2011

(65) Prior Publication Data

US 2011/0276589 A1 Nov. 10, 2011

Related U.S. Application Data

(60) Provisional application No. 61/330,756, filed on May 3, 2010.

(51) Int. Cl.
*G06F 17/30* (2006.01)
(52) U.S. Cl.
USPC .......... 707/769; 707/791; 707/803; 715/513; 715/804; 702/30
(58) Field of Classification Search ........... 707/769, 707/754, 791, 803; 702/27, 32, 30; 715/513, 715/804; 706/20
See application file for complete search history.

(56) References Cited

U.S. PATENT DOCUMENTS

| | | | |
|---|---|---|---|
| 7,707,206 B2 * | 4/2010 | Encina et al. | 707/716 |
| 7,805,437 B1 * | 9/2010 | Andersson et al. | 707/722 |
| 2002/0161599 A1 * | 10/2002 | Faerman et al. | 705/1 |
| 2004/0006742 A1 * | 1/2004 | Slocombe | 715/513 |
| 2004/0236740 A1 * | 11/2004 | Cho et al. | 707/5 |
| 2005/0102313 A1 * | 5/2005 | Levering et al. | 707/102 |
| 2005/0226495 A1 * | 10/2005 | Li | 382/159 |
| 2007/0260583 A1 * | 11/2007 | Domine et al. | 707/3 |
| 2008/0140616 A1 * | 6/2008 | Encina et al. | 707/3 |
| 2008/0228774 A1 * | 9/2008 | Hamilton et al. | 707/10 |
| 2009/0006411 A1 * | 1/2009 | Lele et al. | 707/9 |
| 2009/0171975 A1 * | 7/2009 | McConnell et al. | 707/10 |

OTHER PUBLICATIONS

Tom Jurach,Microsoft Outlook Quick Start Email Guide, Sep. 22, 2006, Microsoft,3 pages.*
International Search Report for PCT Application No. PCT/US2011/035070, mailed Oct. 6, 2011, 4 pages.

(Continued)

*Primary Examiner* — Robert Beausoleil, Jr.
*Assistant Examiner* — Noosha Arjomandi
(74) *Attorney, Agent, or Firm* — Choate Hall & Stewart, LLP

(57) ABSTRACT

In various embodiments, multiple heterogeneous documents are processed to identify structures, such as chemical structures, contained therein, including non-embedded structures. Also described is a graphical user interface that permits a user to search for a structure or substructure within a set of electronic documents, then displays the matching structures as well as the actual pages of the documents on which the matching structures are found. Display of the actual pages allows the user to verify the matches and provides helpful context for the user.

19 Claims, 3 Drawing Sheets

OTHER PUBLICATIONS

Written Opinion for PCT Application No. PCT/US2011/035070, mailed Oct. 6, 2011, 9 pages.

Algorri et al. "Reconstruction of Chemical Molecules from Images," 2007 Annual International Conference of the IEEE Engineering in Medicine and Biology Society (EMBC '07), Lyon, France, Aug. 22-26, 2007, in Conjunction with the Biennial Conference of the Societe Francaise de Genie Biologique et Medical (SFGB), Aug. 22, 2007, pp. 4609-4612.

Casey et al. "Optical Recognition of Chemical Graphics," Document Analysis and Recognition, 1993, Proceedings of the Second International Conference on, Tsukuba Science City, Japan, Oct. 20-22, 1993, Los Alamitos, CA, USA, IEEE Comput. Soc., Oct. 20, 1993, pp. 627-631.

Filippov et al. "Optical Structure Recognition Software to Recover Chemical Information: OSRA, An Open Source Solution," Journal of Chemical Information and Modeling, vol. 49, No. 3, Mar. 23, 2009, pp. 740-743.

Park et al. "Automated extraction of chemical structure information from digital raster images," Chemistry Central Journal, Biomed Central Ltd., vol. 3, No. 1, Feb. 5, 2009, pp. 1-16.

Park et al. "Tunable Machine Vision-Based Strategy for Automated Annotation of Chemical Databases," Journal of Chemical Information and Modeling, vol. 49, No. 8, Aug. 24, 2009, pp. 1993-2001.

Valko et al. "CLiDE Pro: The Latest Generation of CLiDE, a Tool for Optical Chemical Structure Recognition," Journal of Chemical Information and Modeling, vol. 49, No. 4, Apr. 27, 2009, pp. 780-787.

\* cited by examiner

SYSTEMS, METHODS, AND APPARATUS FOR PROCESSING DOCUMENTS TO IDENTIFY STRUCTURES

CROSS-REFERENCE TO RELATED APPLICATION

This application claims priority to and the benefit of, and incorporates herein by reference in its entirety, U.S. Provisional Patent Application No. 61/330,756, which was filed on May 3, 2010.

TECHNICAL FIELD

In various embodiments, the present invention relates to systems, methods, and apparatus for processing documents. More specifically, described herein are exemplary systems, methods, and apparatus that process documents to identify structures, such as chemical structures, contained therein.

BACKGROUND

Over the past several decades, there has been an explosion in the volume and complexity of information available to information consumers. As a result, there is now a large amount of disparate information available in the public domain. Some of this information is buried in, for example, magazines, journals, papers, newspapers, books, textbooks, notebooks, etc. Other information is stored in many different types of digital formats and in many different types of information stores, such as databases, digital libraries, etc.

One field that has seen a tremendous explosion of information over the past several decades is the life sciences field. The primary impediment for a researcher is now not the lack of information, but, rather, the large quantity of information and the unstructured formats used to store that information. For example, a chemical researcher who may wish to search through the above-mentioned sources of information for chemical structures, chemical substructures, and/or chemical reactions of interest faces a daunting task.

A number of computerized technologies exist to aid a chemical researcher in completing this task; however, they are generally of limited value. For example, some technologies are able to search through specific types of documents, such as Microsoft Word documents, for specific types of images, such as object linked and embedded (OLE) images, of molecules. Typically, however, these technologies are unable to systematically process multiple heterogeneous types of documents. In addition, by searching for only specific image types, the approach taken by these technologies is crude and generally results in many molecule images being missed.

As such, a need exists for improved systems, methods, and apparatus for processing documents to identify structures, such as chemical structures, contained therein.

SUMMARY OF THE INVENTION

Described herein are various embodiments of systems, methods, and apparatus that can systematically process data warehouses containing multiple heterogeneous types of documents, such as, for example, Microsoft Word documents, Portable Document Format (PDF) documents, presentations, drawings, etc., and that can convert the drawn images of chemical structures contained within those documents into searchable objects that are linked to the source of the data. Advantageously, in addition to being able to process multiple heterogeneous types of documents, embodiments of the present invention are also able to search for and process multiple heterogeneous types of images within each document or across different types of documents, including both embedded images—such as object linked and embedded (OLE) images—and non-embedded images of chemical structures.

In addition to automatically processing and deciphering graphical representations of chemical structures in a systematic manner, embodiments of the invention described herein are also robust enough to exclude from consideration small graphical shapes (e.g., square tables or text boxes) that might otherwise be mistaken for chemical structures. For example, the systems, methods, and apparatus may filter by criteria to eliminate false positives.

In addition still, embodiments of the present invention provide powerful search tools, which enable an individual to readily access chemical structures, substructures, and/or reactions that would otherwise be buried within hundreds of, thousands of, or even hundreds of thousands of (or more) documents. Such search tools are beneficial to, for example, research managers at pharmaceutical companies, intellectual property attorneys searching through documents for prior art, and others.

In general, in one aspect, embodiments of the invention feature an apparatus for electronically identifying and compiling chemical structures found in a storage facility that stores one or more electronic files. The apparatus includes a memory for storing code defining a set of instructions, and a processor for executing the set of instructions. The code includes an optical structure recognition module that identifies candidate chemical structures in the electronic files of the storage facility and that derives (for each identified candidate) a chemical structure object with an associated set of properties (e.g., number of carbons, number of hetero atoms, number of bonds, number of bonds of a selected bond order, number of rings, and formula weight). The optical structure recognition module also applies (for each derived chemical structure object) one or more filters, including a filter to eliminate objects identified as having less than a selected number of carbons, and stores objects not eliminated by the one or more filters in a searchable electronic compendium of identified objects.

As previously mentioned, the storage facility may include electronic files of two or more different file types (e.g., PDF, Word, Tiff, Excel, Mol File, RXN File, RTF, PowerPoint, cdx, BMP, JPEG, Plain Text, and SDF). In addition, at least one of the electronic files operated upon by the optical structure recognition module may include non-embedded images of chemical structures identifiable by the optical structure recognition module.

In one embodiment, the optical structure recognition module computes (for each derived chemical structure object) a value of a confidence factor based on two or more properties associated with the derived chemical structure object, and eliminates objects based on confidence factor values in order to reduce false positives. For each derived chemical structure object not eliminated by the one or more filters, the optical structure recognition module may associate therewith identification of an electronic document in which the chemical structure is located, and a page or portion thereof on which the chemical structure is located, thereby facilitating identification of the origin of a particular chemical structure or substructure in the one or more electronic files during a search of the electronic compendium for the particular chemical structure or substructure.

In various embodiments, the optical structure recognition module is configured to, for at least one identified candidate chemical structure, derive a chemical structure object with an associated stereochemistry. In certain embodiments, the stereochemistry is identifiable from stereochemistry markings in the original image of the candidate chemical structure, as found in the corresponding electronic file. In other embodiments, the optical structure recognition module attributes the stereochemistry to the chemical structure object based on known rules, for example, priority rules, sequencing rules, and/or naming conventions.

In general, in another aspect, embodiments of the invention feature an apparatus for displaying one or more chemical structures found in an electronic search of a storage facility that stores one or more electronic files. The apparatus includes a memory for storing code defining a set of instructions, and a processor for executing the set of instructions. The code includes a graphical user interface module that displays, in a first designated location of a graphical user interface (GUI) display, one or more chemical structures or substructures derived from an electronic search of a storage facility that stores one or more electronic files. Each of the displayed structures or substructures matches or contains a user-identified chemical structure or substructure. The graphical user interface module also displays, in a second designated location of the GUI display, a list of, and/or icon(s) representing, one or more electronic files from the storage facility. Each such file contains one or more of the structures or substructures displayed in the first designated location of the GUI display. Moreover, the graphical user interface module displays, in a third designated location of the GUI display, a page, or portion thereof, of a selected one of the electronic files listed and/or represented in the second designated location of the GUI display. The displayed page contains a selected one of the chemical structures or substructures displayed in the first designated location of the GUI display.

In various embodiments, at least one of the chemical structures or substructures derived from the electronic search of the storage facility corresponds to a non-embedded image of the chemical structure or substructure in the one or more electronic files. As before, the storage facility may include electronic files of two or more different file types (e.g., PDF, Word, Tiff, Excel, Mol File, RXN File, RTF, PowerPoint, cdx, BMP, JPEG, Plain Text, and SDF).

In general, in another aspect, embodiments of the invention feature a method for electronically identifying and compiling chemical structures found in a storage facility comprising one or more electronic files. The method includes creating and/or downloading electronic files for storage in a storage facility, which may include electronically scanning paper documents in certain embodiments. The method also includes identifying a plurality of candidate chemical structures in the electronic files of the storage facility using an optical structure recognition module, wherein at least one of the electronic files includes non-embedded images of chemical structures identifiable by the optical structure recognition module. For each identified candidate, a chemical structure object with an associated set of properties including number of carbons is derived. For each derived chemical structure object, one or more filters are applied, including a filter to eliminate objects identified as having less than a selected number of carbons. The method then includes storing objects not eliminated by the one or more filters in a searchable electronic compendium of identified objects and displaying results of a user-initiated search of the electronic compendium of identified objects on an electronic display.

In various embodiments, the displaying step includes displaying, in a first designated location of a graphical user interface (GUI) display, one or more of the derived chemical structure objects, wherein each of the displayed objects matches or contains a user-identified chemical structure or substructure. In a second designated location of the GUI display, a list and/or icon(s) representing one or more of the electronic files of the storage facility is displayed, where each displayed file contains (includes) one or more of the derived chemical structure objects displayed in the first designated location of the GUI display. In a third designated location of the GUI display, a page (or portion thereof) is displayed, where the page is from a selected one of the electronic files listed and/or represented in the second designated location of the GUI display, and the page contains a selected one of the chemical structure objects displayed in the first designated location of the GUI display.

In various embodiments, the storage facility contains (includes) a plurality of file types, for example, PDF, Word, Tiff, Excel, Mol File, RXN File, RTF, PowerPoint, cdx, BMP, JPEG, Plain Text, and/or SDF files.

Elements of embodiments described with respect to a given aspect of the invention may be used in various embodiments of another aspect of the invention. For example, it is contemplated that features of dependent claims depending from one independent claim can be used in apparatus and/or methods of any of the other independent claims.

BRIEF DESCRIPTION OF THE DRAWINGS

The foregoing and other objects, aspects, features, and advantages of the invention will become more apparent and may be better understood by referring to the following description taken in conjunction with the accompanying drawings, in which.

DESCRIPTION

In general, in various embodiments, the present invention pertains to systems, methods, and apparatus for processing documents to identify structures contained therein. In broad overview, in accordance with one embodiment of the invention, a user employs a computing system to process one or more documents. In particular, each document is analyzed to identify graphical images contained therein that are suspected to be chemical structures. Once the graphical image of a suspected chemical structure is located, potential chemical structure information is derived therefrom and that information is then stored in a derived chemical structure object (e.g., a computerized representation identifying various atoms, bonds, etc.). As described further below, the derived objects may then be tested and analyzed to ascertain whether or not they are likely to represent true chemical structures. If a derived object is determined to likely be a true chemical structure, that derived object may then be stored, for later use, in a database, together with, optionally, one or more molecular properties. The molecular properties may be derived from the chemical structure itself (e.g., pKa values, formula weight, etc.) and/or may be pulled from external systems, such as external databases. If, on the other hand, the derived object is determined not to be a true chemical structure (or, alternatively, to have a low probability of being a true chemical structure), the derived object is not stored in the database and is instead discarded.

In such a fashion, a global compendium of the true chemical structures contained within one or more documents may be created (e.g., stored as derived objects within a database). The user may then, for example, search the database in order to determine whether or not a particular chemical structure, substructure, reaction, etc. is contained within the document(s).

Figure 1:
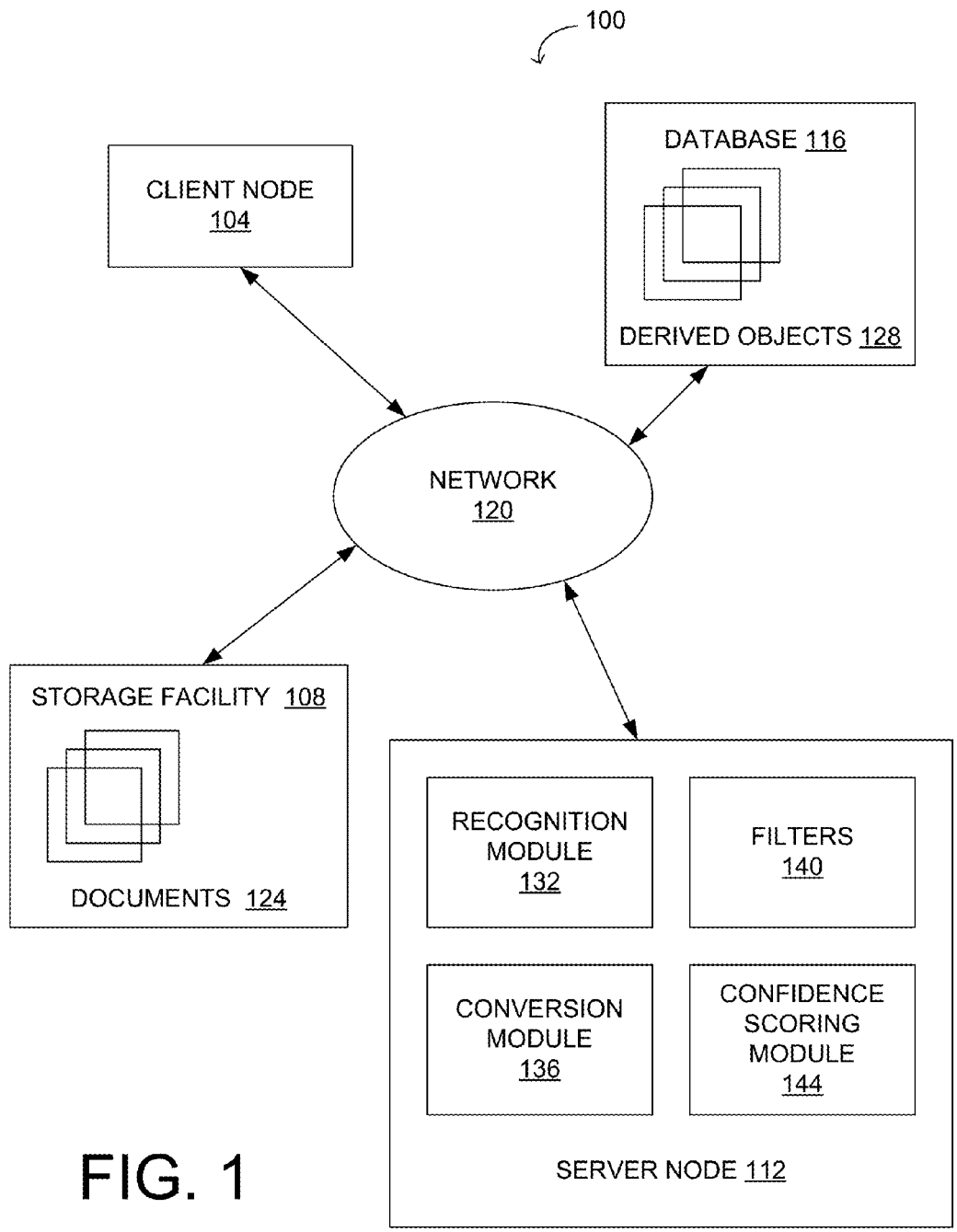
FIG. 1 is a block diagram of a system for processing documents to identify structures contained therein in accordance with an illustrative embodiment of the invention.

FIG. 1 depicts a system 100, according to an illustrative embodiment of the invention, for processing documents to identify chemical structures contained therein. The system 100 includes a client node 104, a storage facility 108, a server node 112, a database 116, and, for enabling communications therebetween, a network 120. As illustrated, the storage facility 108 may store one or more documents 124, and the database 116 may store one or more derived chemical structure objects 128. As also illustrated, the server node 112 may include a recognition module 132, a conversion module 136, one or more filters 140, and a confidence scoring module 144. Although the derived chemical structure objects 128 are only illustrated in FIG. 1 as being stored in the database 116, in one embodiment, as described below, the server node 112 generates the derived chemical structure objects 128 and, as such, may store those derived objects 128 at the server node 112 for a period of time.

The network 120 may be, for example, a local-area network (LAN), such as a company Intranet, a metropolitan area network (MAN), or a wide area network (WAN), such as the Internet. Each of the client node 104, storage facility 108, server node 112, and database 116 may be connected to the network 120 through a variety of connections including, but not limited to, standard telephone lines, LAN or WAN links (e.g., T1, T3, 56 kb, X.25), broadband connections (e.g., ISDN, Frame Relay, ATM), or wireless connections. The connections, moreover, may be established using a variety of communication protocols (e.g., HTTP, TCP/IP, IPX, SPX, NetBIOS, NetBEUI, SMB, Ethernet, ARCNET, Fiber Distributed Data Interface (FDDI), RS232, IEEE 802.11, IEEE 802.11a, IEEE 802.11b, IEEE 802.11g, and direct asynchronous connections).

The client node 104 may be any type of personal computer, Windows-based terminal, network computer, wireless device, information appliance, RISC Power PC, X-device, workstation, mini computer, main frame computer, personal digital assistant, set top box, handheld device, or other computing device that is capable of both presenting information/data to, and receiving commands from, a user of the client node 104. The client node 104 may include, for example, a visual display device (e.g., a computer monitor), a data entry device (e.g., a keyboard), persistent and/or volatile storage (e.g., computer memory), a processor, and a mouse. In one embodiment, the client node 104 includes a web browser, such as, for example, the INTERNET EXPLORER program developed by Microsoft Corporation of Redmond, Wash., to connect to the World Wide Web.

For its part, the server node 112 may be any computing device that is capable of receiving information/data from and delivering information/data to the client node 104, for example over the network 120, and that is capable of querying, receiving information/data from, and delivering information/data to the storage facility 108 and/or database 116. For example, as further explained below, the server node 112 may obtain a document 124 from the storage facility 108, operate upon the document 124 so as to create one or more derived objects 128, and transmit the derived object(s) 128 to the database 116 for storage thereat. The server node 108 may include a processor and persistent and/or volatile storage, such as computer memory.

The storage facility 108 may be any computing device that is capable of receiving commands/queries and information/data from, and delivering information/data to, the server node 112 and/or client node 104. In one embodiment, the storage facility 108 stores documents 124, such as, for example, Microsoft Word documents, Microsoft Excel documents, Microsoft PowerPoint documents, Portable Document Format (PDF) documents, Tagged Image File Format (TIFF) documents, Rich Text Format (RTF) documents, Plain Text documents, Bitmap Image File Format (BMP) documents, Joint Photographic Experts Group (JPEG) documents, documents having the filename extensions .mol, .rxn, .cdx, or .sdf, or any other type of electronic document. The documents 124 may contain, for example, object linked and embedded (OLE) images, or otherwise embedded images, of chemical structures. In addition, or in the alternative, the documents 124 may contain non-embedded images of chemical structures.

For its part, the database 116 may be any computing device that is capable of receiving commands/queries and information/data from, and delivering information/data to, the server node 112 and/or client node 104. In one embodiment, the database 116 stores and manages collections of data, such as the derived objects 128. Both the storage facility 108 and the database 116 may communicate using SQL or another language, or may use other techniques to store, receive, and transmit data.

The recognition module 132, conversion module 136, one or more filters 140, and confidence scoring module 144 of the server node 112 may each be implemented as any software program and/or hardware device, for example an application specific integrated circuit (ASIC) or a field programmable gate array (FPGA), that is capable of providing the functionality described below. It will be understood by one having ordinary skill in the art that the illustrated modules, filters, and organization of the server node 112 are conceptual, rather than explicit, requirements. For example, any two or more of the illustrated modules (e.g., the recognition module 132 and the conversion module 136) may be combined into a single module, such that the functions performed by the two or more modules, as described below, are in fact performed by the single module. In addition, it should be understood that any single one of the illustrated modules may in fact be implemented as multiple modules, such that the functions performed by the single module, as described below, are in fact performed by the multiple modules. In one particular embodiment, the functionality of any one or more of (or portions of) the recognition module 132, the conversion module 136, the filters 140, and the confidence scoring module 144 is performed by a single module, termed an optical structure recognition module.

Although not shown, each of the client node 104, the storage facility 108, the server node 112, and the database 116 may also include its own transceiver (or separate receiver and transmitter) that is capable of receiving and transmitting communications, including requests, responses, and commands, such as, for example, inter-processor communications and networked communications. The transceivers (or separate receivers and transmitters) may each be implemented as a hardware device, or as software module with a hardware interface.

It will be understood by those skilled in the art that FIG. 1 is a simplified illustration of the system 100 and that it is depicted as such to facilitate the explanation of the present invention's embodiments. Moreover, the system 100 may be modified in of a variety of manners without departing from the spirit and scope of the invention. For example, rather than all being implemented on a single server node 112, one or more of the illustrated modules or filters may instead be implemented on one or more other computing devices (not shown) and such computing devices may communicate with one another directly, over the network 120, or over another additional network (not shown). In addition, the documents 124 illustrated as being stored by the single storage facility 108 may in fact be stored across multiple storage facilities 108 in a storage area network (SAN). Similarly, the collections of data stored and managed by the database 116 may in fact be stored and managed by multiple databases (not shown). In yet another example, the functionality of either or both the storage facility 108 and the database 116 may in fact be resident on the server node 112. In particular, the documents 124 and/or derived objects 128 may be stored in the same (or different) memory present on the server node 112. Another option is for the storage facility 108, the server node 112, and the database 116 to be local to the client node 104, such that they may all communicate directly without using the network 120. Alternatively, the functionality the storage facility 108, the server node 112, the database 116, and the modules/filters shown as being implemented on the server node 112 may in fact each be implemented on the client node 104. As such, the depiction of the system 100 in FIG. 1 is non-limiting.

Figure 2:
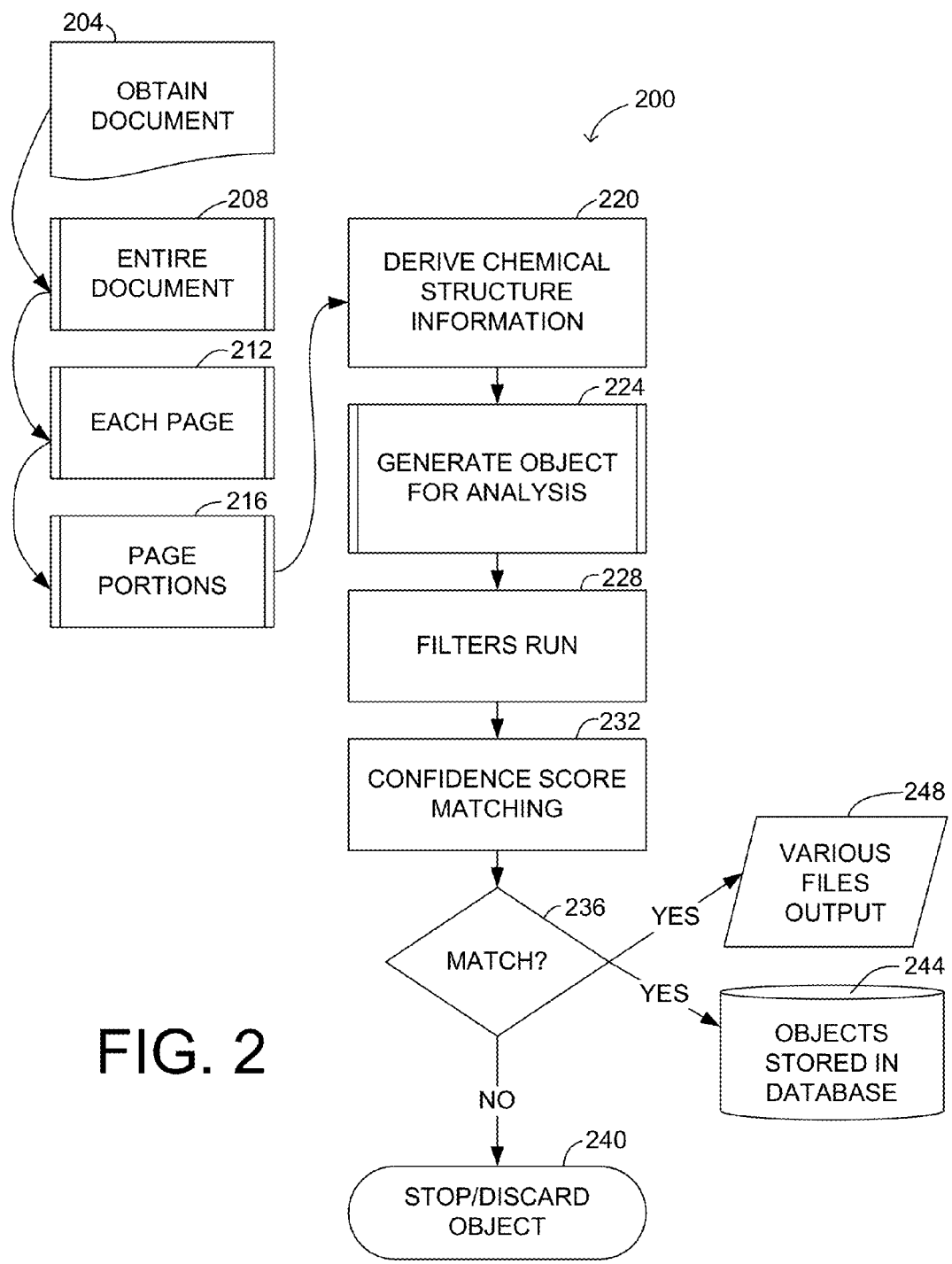
FIG. 2 is a flow diagram of a method for processing documents to identify structures contained therein in accordance with an illustrative embodiment of the invention.

With reference now to FIG. 2, in one illustrative embodiment of a method 200 for processing a document to identify chemical structures contained therein, for example using the system 100 of FIG. 1, the document 124 is first obtained at step 204. Graphical images of suspected chemical structures are then located in the document 124 at steps 208, 212, and 216. Potential chemical structure information is then derived from each graphical image of a suspected chemical structure at step 220, and a derived object 128, storing that chemical structure information, is created at step 224 (at this point, the derived object 128 may be stored in the computer memory of the server node 112, rather than in the database 116 as illustrated in FIG. 1). One or more filters 228 are then employed at step 228 to remove from consideration those derived objects 128 that are not likely to represent true chemical structures. A confidence score is then calculated at step 232 for each derived object 128 that is not discarded by one of the filters 228. If, at step 236, it is determined that the confidence score indicates that a derived object 128 is not likely to be a true chemical structure, that derived object 128 is simply discarded at step 240. If, on the other hand, it is determined at step 236 that the confidence score indicates a derived object 128 is likely to be a true chemical structure, that derived object 128 is then stored, at step 244, in the database 116 together with, optionally, one or more molecular properties. In addition, the derived object 128 may be employed in creating and outputting, at step 248, one or more files.

In greater detail, and with reference to FIGS. 1 and 2, the server node 112 first obtains a document 124 from the storage facility 108 at step 204. For example, the server node 112 may query the storage facility 108 for the document 124 of interest, and, in response to that query, the storage facility 108 may transmit the document 124 to the server node 112. If the document 124 isn't pre-stored in the storage facility 108 (e.g., a user has a physical manual that he or she wants to search for particular chemical structures of interest), the document 124 may first be scanned or downloaded for storage in the storage facility 108, and thereafter be obtained by the server node 112.

Once the server node 112 has obtained the document 124, the recognition module 132 may be employed to locate, in the document 124, graphical images of suspected chemical structures. More particularly, at step 208, the recognition module 132 first scans the document 124 in its entirety (without page breaks), thereby generating a large stream of data. Embedded objects may then be extracted from the data stream and run through a file filter to see if the embedded objects match known MIME types that are typically found in documents relating to chemistry. If not, the embedded objects may be discarded. If, on the other hand, the embedded objects do match known MIME types that are typically found in documents relating to chemistry, the embedded objects may be dealt with separately, as discussed below. With the embedded objects removed from the data stream, the data stream is then processed to locate discrete non-embedded graphical images, which are then suspected to be chemical structures. In particular, known grayscale and binarization algorithms, segmentation algorithms, anisotropic smoothing and thinning algorithms, and/or vectorization algorithms may be run on the data stream in order to locate the discrete non-embedded graphical images that are candidate chemical structures. The recognition module 132 may then store all such located non-embedded graphical images in the computer memory (e.g., in a temporary directory) of the server node 112.

Then, at step 212, the recognition module 132 scans each page of the document 124, thereby generating a new stream of data for each page. Each such stream may then be processed to locate discrete non-embedded graphical images that are candidate chemical structures. As before, known grayscale and binarization algorithms, segmentation algorithms, anisotropic smoothing and thinning algorithms, and/or vectorization algorithms may be run on each data stream in order to locate the discrete non-embedded graphical images contained therein, which the recognition module 132 may then store as suspected chemical structures in the computer memory of the server node 112.

At step 216, each page of the document 124 is then broken down into multiple segments or quadrants (first into quarters, then into eighths, then into 16ths, and so on down to a size that is, for example, just larger than a quarter inch by quarter inch square to help prevent characters, such as Kanji characters or Chinese text, from being mistaken for chemical structures). Each such segment or quadrant (i.e., each quarter, each eighth, each 16th, etc.) may then be separately processed to locate discrete non-embedded graphical images. Again, known grayscale and binarization algorithms, segmentation algorithms, anisotropic smoothing and thinning algorithms, and/or vectorization algorithms may be run on each segment or quadrant in order to locate the discrete non-embedded graphical images contained therein, which the recognition module 132 may then store as suspected chemical structures in the computer memory of the server node 112. Redundant suspected chemical structures identified in steps 208, 212, and 216 may then be eliminated. In addition, for a given suspected chemical structure, the level of redundancy over the various steps 208, 212, and 216 may be a variable in the confidence factor calculated at step 232, explained below.

The embedded objects that were extracted from the document 124 at step 208 and that were found to match known MIME types typically found in documents relating to chemistry are then treated in one of two ways. First, if an embedded object itself contains a molecule connection table (as described below with reference to step 224), a derived object 128 may be created directly therefrom. More specifically, the molecule connection table may be passed directly to step 224 of the method 200 to generate a derived object 128 thereat (i.e., step 220 of the method 200 is skipped for the embedded object containing that molecule connection table). Alternatively, in the second case, if the embedded object fails to contain a molecule connection table, the embedded object is itself unembedded and is treated as a data stream. That data stream may then processed as described above to locate discrete graphical images. In particular, known grayscale and binarization algorithms, segmentation algorithms, anisotropic smoothing and thinning algorithms, and/or vectorization algorithms may be run on the data stream in order to locate the discrete graphical images, which the recognition module 132 may then store as suspected chemical structures in the computer memory of the server node 112.

At step 220, once the graphical images of suspected chemical structures are located and stored in the computer memory of the server node 112, potential chemical structure information may be derived from each such graphical image. In particular, the recognition module 132 may interpret each line in a graphical image as a bond and the points where two lines join as carbon atoms. Two parallel lines, for example, may be interpreted as a double-bond, and three parallel lines may be interpreted as a triple-bond. The recognition module 132 may also employ optical character recognition to identify and recognize non-carbon atoms. In essence, as will be understood by one of ordinary skill in the art, the recognition module 132 may detect and derive nodes, single bonds, double bonds, triple bonds, bridge bonds, atomic labels, charges, circle bonds (for old style aromatic rings), 5-member rings, 6-member rings, the number of atoms in the largest ring, the number of carbons, the number of di-substituted carbons (i.e., no branched carbon), the number of tri-substituted carbons (i.e., single branched carbon), the number of tetrahedral carbons (i.e., saturated branched carbon), the number of stereocenters, and special bonds indicating stereochemistry (e.g., wedge and dash bonds).

In one embodiment, if the graphical image contains flat lines with no stereochemistry defined, the recognition module 132 analyzes sets of candidate bonds that can represent a tetrahedral center in order to determine if the bond center in fact contains a stereo chemical configuration. If so, the recognition module 132 can assign the correct stereo chemical configuration to the bond center.

At step 224, the conversion module 136 may create a derived object 128 for each graphical image of a suspected chemical structure that was located at steps 208, 212, and 216. In one embodiment, each derived object 128 stores the chemical structure information that was derived from its corresponding graphical image at step 220. Each derived object 128 may feature, for example, a standardized molecule connection table of the type found in a chemical table file, which is well known to those of ordinary skill in the art. Briefly, such a molecule connection table contains information about a chemical structure, such as information about the atoms, bonds, connectivity, and coordinates of the molecule. For example, the molecule connection table may indicate the number of carbon atoms, the number of hetero atoms, the number of bonds, the number of bonds of a selected bond order, the number of rings, and/or the formula weight of a particular molecule. In one embodiment, the molecule connection tables are converted into a series of standardized file formats for compatibility, such as, for example, SMILES strings, InChI strings, .mol files, and .CDX files.

Following the creation of derived objects 128 by the conversion module 136 at step 224, one or more filters 140 may be applied to each such derived object 128 as an aid towards determining whether or not the particular derived object 128 under consideration represents a true chemical structure. For example, a minimum number of carbon atoms filter 140 may be employed to eliminate derived objects 128 that are not likely to represent true chemical structures. More specifically, in some instances the recognition module 132 and the conversion module 136, when employing the methodology described above, will mistakenly recognize and convert square tables and text boxes into cyclobutane (i.e., a molecule having four single bonds and four carbon atoms). In order to eliminate such invalid structures and other invalid structures, the minimum number of carbon atoms filter 140 may be set to discard any derived object 128 having less than a certain number of carbon atoms. In one embodiment, the minimum number of carbon atoms is configurable and is set by the user based on the expected content of the document 124. The minimum number of carbon atoms may default to, for example, eight.

In addition to square tables and text boxes, the recognition and conversion modules 132, 136 may also mistakenly recognize and convert other common shapes in a document 124 into chemical structures. For example, parallel lines on a page may be misrepresented as ethylene gas. Accordingly, additional filters 140 may be applied to the derived objects 128 to further aid in determining whether or not the derived objects 128 represent true chemical structures. As examples, the additional filters 140 may filter out each derived object 128 having less than a minimum number of hetero atoms (e.g., nitrogen, oxygen, phosphorus, chlorine, bromine, etc. atoms), less than a minimum number of bonds, less than a minimum number of bonds with a certain bond order (e.g., single bonds, double bonds, triple bonds), less than a minimum number of rings, less than a minimum number of di-substituted carbons, less than a minimum number of tri-substituted carbons, less than a minimum number of tetra-substituted carbons, less than a minimum number of wedge bonds, and/or less than a minimum formula weight. Again, the minimum threshold of each filter 140 may be configurable and be set by the user based on the expected content of the document 124. In addition, all filters 140 may be applied to each derived object 128, or the user may configure the system 100 to apply select combinations of the filters 140 (e.g., subsets of all the filters 140) to the derived objects 128 based, again, on the expected content of the document 124. In each case, a filter 140 can determine whether or not a derived object 128 should be filtered out as an invalid structure by inspecting the derived object's molecule connection table and/or, if desirable, by pulling additional information from external databases to supplement the information contained within the molecule connection table.

Exemplary filters 140 that may be employed at step 228 include those that determine whether a derived object 128 contains any one of the following (with the numbers set forth between the "{ }" brackets being configurable by the user):
  at least {8} carbon atoms; or
  at least one {1} heteroatom and a minimum of four {4} carbon atoms; or
  at least one {1} ring and one {1} double bond; or
  [(at least one {1} tetra-substituted carbon or one {1} tri-substituted carbon atom)] and [(a minimum of four {4} carbon atoms) or (one {1} ring) or (one {1} heteroatom)]; or
  (at least two {2} double bonds) or (one {1} double bond and one {1} triple bond); or
  at least four {4} carbon atoms and one {1} heteroatom labeled with (R or X); or at least one {1} wedge bond from one {1} di-substituted carbon center.

Once the filters 140 have eliminated, at step 228, certain derived objects 128 that are not likely to represent true chemical structures, the confidence scoring module 144 may be employed at step 232 in order to ascertain the confidence that each remaining derived object 128 is not, in fact, an artifact that was present on a page of the document 124. In one embodiment, the confidence scoring module 144 calculates, for each remaining derived object 128, a confidence factor according to the following formula:

$$\text{Confidence} = 0.316 - 0.0163 * Nc + 0.0343 * Nn + 0.0668 * No + 0.03657 * Nf + 0.06555 * Ns + 0.0668 * Ncl - 0.2127 * Nrings + 0.0713 * Naromatic + 0.3299 * Nrings5 + 0.34286 * Nrings6 - 0.037796 * Nfragments$$

where, Nc is the number of carbon atoms in the molecule connection table of the derived object 128, Nn is the number of nitrogen atoms therein, No is the number of oxygen atoms therein, Nf is the number of fluorine atoms therein, Ns is the number of sulfur atoms therein, Ncl is the number of chlorine atoms therein, Nrings is the number of rings therein, Naromatic is the number of aromatic rings therein, Nrings5 is the number of 5-member rings therein, Nrings6 is the number of 6-member rings therein, and Nfragments is the number of reactive fragments (i.e., parts of a real molecule) therein. In one embodiment, a set of known reactive fragments is stored in the database 116, and the confidence scoring module 144 compares the contents of the derived object's molecule connection table to the reactive fragments stored in the database 116 in order to determine the value of Nfragments.

In one embodiment, where the calculated confidence factor for a derived object 128 is greater than or equal to 0.25, the confidence scoring module 144 determines, at step 236, that the derived object 128 is likely to represent a true chemical structure. On the other hand, where the calculated confidence factor for a derived object 128 is less than 0.25, the confidence scoring module 144 determines, at step 236, that the derived object 128 is likely to be an artifact, and the derived object 128 is discarded at step 240. As before, the confidence factor may be user-configurable, such that thresholds other than 0.25 may be employed.

In addition to, and/or in the alternative to one or more of, the variables set forth in the confidence factor formula set forth above, the confidence factor may also be a function of other variables, such as, for example, the number of double bonds, the number of triple bonds, the number of atoms in the largest ring, the number of stereocenters, the number of di-substituted carbons (i.e., no branched carbon), the number of tri-substituted carbons (i.e., single branched carbon), and the number of tetrahedral carbons (i.e., saturated branched carbon).

In one embodiment, where a derived object 128 is determined, at step 236, to likely represent a true chemical structure, the derived object 128 is stored, at step 244, in the database 116. In doing so, additional information may, optionally, be associated with the derived object 128. For example, the derived object 128 may be associated with the particular location in the document 124 at which its corresponding graphical image was found. This may be done, for example, by using a relational table in the database 116 that links each derived object 128 and document 124 location along with a globally unique identifier (GUID) for quick reference. In addition, an image file or thumbnail of the chemical structure that the derived object 128 represents may also be stored in the database 116 and be associated (e.g., linked via the relational table) to the derived object 128. Then, when a user searches the database 116, as described below, the image file or thumbnail may be presented to the user as part of the search results. Moreover, molecular properties derived from the chemical structure itself (e.g., pKa values, formula weight, etc.) and/or pulled from external systems, such as external databases, a corporate registry, and/or a corporate inventory, may be associated with (e.g., added to and stored with) the derived object 128 that represents that chemical structure. Registration numbers, serial numbers, lot numbers, batch codes, or any other information for the chemical structure of interest pulled from the external systems may also be associated with each derived object 128 and its associated document 124.

Finally, at step 248, the server node 112 may employ one or more derived objects 128 in creating and outputting one or more files.

It will be understood that while the steps of the method 200 are described herein as occurring in series and in the order presented, certain steps may in fact occur in a different order or be executed in parallel with other steps. For example, while the method 200 has been described with reference to the system 100 to operate upon a single document 124, the system 100 may in fact operate upon multiple documents 124 at once, such that different steps of the method 200 are performed concurrently for different documents 124. In addition, while each step of the method 200 has been described to complete operation upon all graphical images, derived objects 128, etc. located in or associated with a single document 124 before the next step is commenced, different steps of the method 200 may instead concurrently process different graphical images, derived objects 128, etc. located in or associated with a single document 124. For example, some derived objects 128 may be filtered at step 228, while other derived objects 128 are at the same time confidence scored at step 232. As such, the particular flow indicated for the method 200 in FIG. 2 is non-limiting.

In one embodiment, once one or more documents 124 have been processed, as described above, to identify the chemical structures contained therein, a user may employ an application, such as a web-based application, present on the client node 104 to search the one or more documents 124 for chemical structures of interest. Alternatively, the user may specify the chemical structure to be searched in a document 124 prior to that document 124 being processed as described above. In this latter case, the document 124 may then be processed via the entire method 200 before the search results are returned, or the method 200 may be modified to focus only on the particular chemical structure being searched for. For example, the method 200 may be modified to end at step 224, and, at that point, those derived objects 128 having molecule connection tables satisfying the user's search criteria may be stored in the database 116 and returned to the user as search results. Effectively, this search method would discard all structures not searched for by the user, rather than only those structures that are filtered out by the filters 140 or discarded by the confidence scoring module 144. The manner in which the document 124 is processed (i.e., whether the entire method 200 is run, or only a portion thereof) may, for example, be a user-configurable option that is selected by the user at the time of interacting with the search application.

The search application may permit the user of the client node 104 to, for example, search for particular chemical structures, chemical substructures, and/or chemical reactions. The search request may be input in a variety of manners, for example by the user entering the textual name of, or graphically drawing on a portion of the search application screen, the chemical structure, chemical substructure, and/or chemical reaction. The search application may then query the database 116 for the derived object(s) 128 matching the user's search query. The search application may query the database 116 in any manner. For example, the search application may generate a number of "synonyms" to the search request entered by the user and employ these synonyms in addition to, or in the alternative to, the user's search request in querying the database 116. For example, where the user has entered the textual name of a chemical structure or substructure in his or her search request, the search application may generate synonyms such as the chemical structure's or substructure's formula, its molecular weight, etc., and employ these synonyms in querying the database 116.

Figure 3:
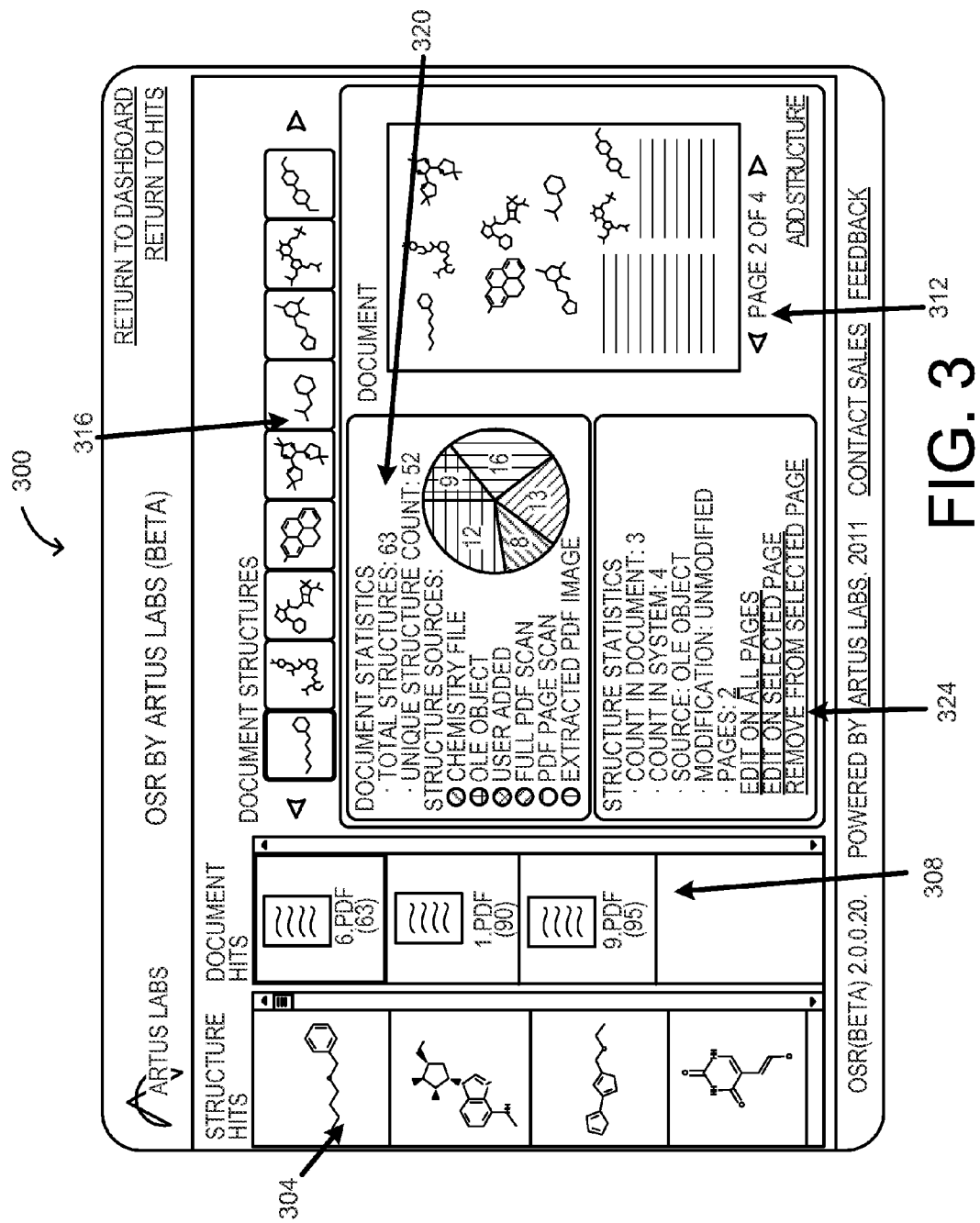
FIG. 3 is a screenshot of a graphical user interface that displays search results, and other information, returned by a search application in accordance with an illustrative embodiment of the invention.

FIG. 3 depicts a screenshot of a graphical user interface 300 that displays the search results, and other information, returned by the search application, in accordance with one embodiment of the invention, after querying the database 116. As illustrated, the graphical user interface 300 includes six sections, although one of ordinary skill in the art will understand that the search application can be configured such that the graphical user interface 300 includes fewer or more sections. In addition, the sections may be arranged in any layout, and have any size. In the illustrated embodiment, a first section 304 of the graphical user interface 300 is a hit list displaying one or more chemical structures of substructures that match or contain the chemical structure or substructure identified by the user in his or her search request. In one embodiment, the hit list 304 drives the other sections of the graphical user interface 300. More specifically, when the user selects a chemical structure or substructure in the hit list 304, the search application loads data associated with that selected structure or substructure in the other sections of the graphical user interface 300. In one embodiment, at least one of the chemical structures or substructures displayed in the first section 304 corresponds to a non-embedded image of the chemical structure or substructure in one or more of the documents 124 stored in the storage facility 108.

A second section 308 of the graphical user interface 300 displays a list of, and/or icons representing, one or more of the documents 124 contained within the storage facility 108 that include one or more graphical images of the chemical structure or substructure selected in the hit list 304. As previously mentioned, the list and/or icons are produced and displayed in the second section 308 when the user selects a chemical structure or substructure in the hit list 304. As illustrated, each document 124 identified in the second section 308 may also include, in brackets, a number identifying how many other chemical structures and/or substructures are contained within that document 124.

A third section 312 of the graphical user interface 300 displays a page, or portion thereof, of a document 124 at which the chemical structure or substructure selected in the hit list 304 was found. That portion of the document 124 is displayed in the third section 312 when the user selects the document 124 in the second section 308. The third section 312 of the graphical user interface 300 also includes navigation aids (e.g., arrows) to advance or retreat through the document 124 from one page to the next. In one embodiment, the third section 312 is interactive. For example, it allows a user to edit or delete portions of the document 124 that he or she believes to be incorrect.

A fourth section 316 of the graphical user interface 300 provides a list of, and/or a series of graphical images of, chemical structures and/or substructures that are contained in the document 124 displayed in the third section 312. In certain embodiments, the list scrolls horizontally and/or has a pop up zoom viewer. A fifth section 320 of the graphical user interface 300 displays statistical information about the type of chemical structures and/or substructures found in the search (e.g., the total number of chemical structures and/or substructures found, the number of unique chemical structures and/or substructures found, etc.), and about where the chemical structures and/or substructures were found (e.g., in a chemistry file, in an OLE object, in a PDF document, etc.). Finally, a sixth section 324 of the graphical user interface 300 displays information about the chemical structure or substructure selected in the first section 304 of the graphical user interface 300 and about how that chemical structure or substructure relates to the document 124 selected in the second section 308 of the graphical user interface 300. For example, the sixth section 324 identifies how many times the chemical structure or substructure selected in the first section 304 appears in the document 124 selected in the second section 308 and in other documents 124 stored in the storage facility 108. In one embodiment, the sixth section 324 also provides links to tools allowing the user to edit the document 124 selected in the second section 308 and thereby displayed in the third section 312 of the graphical user interface 300.

Accordingly, it can readily be seen that embodiments of the present invention provide a robust and powerful search application, in addition to providing systems, methods, and apparatus that can systematically process multiple heterogeneous types of documents stored within the storage facility 108.

It should also be noted that embodiments of the present invention may be provided as one or more computer-readable programs embodied on or in one or more articles of manufacture. The article of manufacture may be any suitable hardware apparatus, such as, for example, a floppy disk, a hard disk, a CD ROM, a CD-RW, a CD-R, a DVD ROM, a DVD-RW, a DVD-R, a flash memory card, a PROM, a RAM, a ROM, or a magnetic tape. In general, the computer-readable programs may be implemented in any programming language. Some examples of languages that may be used include C, C++, or JAVA. The software programs may be further translated into machine language or virtual machine instructions and stored in a program file in that form. The program file may then be stored on or in one or more of the articles of manufacture.

Certain embodiments of the present invention were described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

What is claimed is:

1. An apparatus for electronically identifying and compiling chemical structures found in a storage facility comprising one or more electronic files, the apparatus comprising:
    (a) a memory for storing a code defining a set of instructions; and
    (b) a processor for executing the set of instructions, wherein the instructions, when executed by the processor, cause the processor to:

(i) identify a plurality of candidate chemical structures in at least a portion of the one or more electronic files of the storage facility, wherein
each electronic file of the portion of the one or more electronic files comprises at least one respective non-embedded image of a chemical structure, and
identifying a respective candidate chemical structure comprises identifying one or more graphical features common to chemical structures;
(ii) for each candidate chemical structure of the plurality of candidate chemical structures, derive a respective chemical structure object with an associated set of properties, wherein
one or more properties of the set of properties is derived from at least a portion of the one or more graphical features common to chemical structures,
a first property of the set of properties is a number of carbons, wherein the number of carbons is derived from the one or more graphical features common to chemical structures, and
a second property of the set of properties comprises one of the following: (A) number of hetero atoms, (B) number of bonds, (C) number of bonds of a selected bond order, (D) number of rings, and (E) formula weight;
(iii) for each chemical structure object, apply one or more filters to at least one property of the associated set of properties, wherein
the one or more filters includes a filter configured to eliminate chemical structure objects having a value of the first property of the set of properties less than a predetermined number of carbons;
(iv) for each chemical structure object, compute a respective confidence factor value based on two or more properties of the set of properties associated with the chemical structure object; wherein
one or more chemical structure objects are eliminated based on respective confidence factor values in order to reduce false positives; and
(v) provide, for storage in a searchable electronic compendium of identified chemical structure objects, chemical structure objects not eliminated by the one or more filters.

2. The apparatus of claim 1, wherein the storage facility comprises a plurality of electronic files of two or more different file types.

3. The apparatus of claim 2, wherein the two or more different file types comprise at least two members selected from the group consisting of PDF, Word, Tiff, Excel, Mol File, RXN File, RTF, PowerPoint, cdx, BMP, JPEG, Plain Text, and SDF.

4. The apparatus of claim 1, wherein the instructions cause the processor to, after applying the one or more filters, for each remaining chemical structure object, associate therewith identification of a respective electronic document in which the candidate chemical structure from which the respective chemical structure object was derived is located, and a page or portion thereof on which the candidate chemical structure is located, thereby facilitating identification of the origin of a particular chemical structure or substructure in the one or more electronic files during a search of the electronic compendium for the particular chemical structure or substructure.

5. The apparatus of claim 1, wherein, for at least one candidate chemical structure of the plurality of candidate chemical structures, a third property of the set of properties associated with a respective chemical structure object derived therefrom comprises stereochemistry.

6. The apparatus of claim 1, wherein the instructions, when executed, further cause the processor to:
(v) responsive to a search query, provide, for viewing by a user at a display device; graphical user interface information, wherein the graphical user interface (GUI) information is configured, upon presentation, to provide:
(a) in a first designated location of a graphical user interface, one or more matching chemical structures, wherein
each of the one or more matching chemical structures corresponds to a respective chemical structure object in the searchable electronic compendium of identified chemical structure objects, and
each of the one or more matching chemical structures comprises a selectable control configured, upon selection, to present information pertaining to the respective matching chemical structure,
(b) in a second designated location of the graphical user interface, one or more selectable controls representing one or more electronic files from the storage facility, wherein each file of the one or more electronic files comprises at least one of the one or more matching chemical structures, and
(c) in a third designated location of the graphical user interface, a portion of a particular electronic file of the one or more electronic files, wherein the portion of the particular electronic file comprises at least one of the one or more matching chemical structures.

7. The apparatus of claim 1, wherein the each chemical structure object comprises a standardized molecule connection table.

8. The apparatus of claim 7, wherein a format of the standardized molecule connection table is compatible with a standardized chemical table file type.

9. A method for automated identification of graphical representations of chemical structures comprising:
identifying, by a processor of a computing device, within an electronic file comprising one or more non-embedded images of chemical structures, at least one candidate chemical structure, wherein the at least one candidate chemical structure is identified based at least in part on graphical image processing, wherein the graphical image processing comprises identifying one or more graphical features common to chemical structures;
for each of the at least one candidate chemical structure, deriving, by the processor, a respective chemical structure object, wherein
the respective chemical structure object comprises a set of properties, wherein
one or more properties of the set of properties is derived from at least a portion of the one or more graphical features common to chemical structures,
a first property of the set of properties is a number of carbons, and
a second property of the set of properties comprises one of the following: (A) number of hetero atoms, (B) number of bonds, (C) number of bonds of a selected bond order, (D) number of rings, and (E) formula weight;
for each chemical structure object, applying, by the processor, one or more filters, wherein
each filter of the one or more filters is configured to compare one or more properties of the set of properties of a given chemical structure object to one or more predetermined values, and a first filter of the one or more filters is configured to eliminate chemical structure objects based at least in part on a determination that the chemical structure object has fewer than a predetermined number of carbons;

for each chemical structure object, calculating a respective confidence factor value based on two or more properties of the set of properties associated with the chemical structure object, wherein
- each chemical structure of the at least one confirmed chemical structure is identified based at least in part upon respective confidence score associated with the respective chemical structure object derived therefrom; and identifying, by the processor, at least one confirmed chemical structure, wherein each chemical structure of the at least one confirmed chemical structure is identified based at least in part upon the respective chemical structure object derived therefrom avoiding elimination by the one or more filters.

10. The method of claim 9, wherein:
calculating the confidence score comprises applying a formula to at least three properties of the respective set of properties, wherein
- the respective set of properties comprises two or more of number of nitrogen atoms, number of oxygen atoms, number of fluorine atoms, number of sulfur atoms, number of chlorine atoms, number of rings, number of aromatic rings, number of five-member rings, number of six-member rings, and number of reactive fragments.

11. The method of claim 9, wherein identifying the one or more non-embedded images of chemical structures comprises, for each page of the electronic file, successively segmenting the respective page into greater number of segments and identifying suspected chemical structures within each segment.

12. The method of claim 9, further comprising, for each confirmed chemical structure:
deriving molecular properties of the respective chemical structure, wherein
- the molecular properties are accessed from a database, corporate registry, or corporate inventory system; and
associating the molecular properties with the respective chemical structure.

13. The method of claim 9, further comprising:
receiving a query comprising a specified chemical structure, wherein
- applying the one or more filters comprises comparing the set of properties of a given chemical structure object to a plurality of known chemical properties of the chemical structure, and
- identifying at least one confirmed chemical structure comprises identifying the at least one confirmed chemical structure as a suspected match to the specified chemical structure.

14. A non-transitory computer-readable medium having instructions stored thereon, wherein the instructions, when executed by a processor, cause the processor to:
identify, within an electronic file comprising one or more non-embedded images of chemical structures, at least one candidate chemical structure, wherein the at least one candidate chemical structure is identified based at least in part on graphical image processing, wherein
- the graphical image processing comprises identifying one or more graphical features common to chemical structures;

for each of the at least one candidate chemical structure, derive a set of properties, wherein
- one or more properties of the set of properties is derived from at least a portion of the one or more graphical features common to chemical structures,
- a first property of the set of properties is a number of carbons, and
- a second property of the set of properties comprises one of the following: (A) number of hetero atoms, (B) number of bonds, (C) number of bonds of a selected bond order, (D) number of rings, and (E) formula weight;

for each candidate chemical structure, apply one or more filters, wherein
- each filter of the one or more filters is configured to compare one or more properties of the set of properties of a given candidate chemical structure to one or more predetermined values, and
- a first filter of the one or more filters is configured to eliminate candidate chemical structures based at least in part on a determination that the given candidate chemical structure has fewer than a predetermined number of carbons;

for each chemical structure object, calculate a respective confidence factor value based on two or more properties of the set of properties associated with the chemical structure object, wherein
- each chemical structure of the at least one confirmed chemical structure is identified based at least in part upon respective confidence score associated with the respective chemical structure object derived therefrom; and identify at least one confirmed chemical structure, wherein each chemical structure of the at least one confirmed chemical structure is identified based at least in part upon the candidate chemical structure avoiding elimination by the one or more filters.

15. The computer-readable medium of claim 14, wherein the instructions, when executed, further cause the processor to, for each confirmed chemical structure:
associate a respective electronic document in which the respective confirmed chemical structure is located and a respective location within the respective electronic document, wherein
- the respective location identifies a location of the confirmed chemical structure.

16. The computer-readable medium of claim 15, wherein the respective position comprises a page number.

17. The computer-readable medium of claim 15, further comprising:
causing presentation of, on a display of a user device,
- (i) in a first designated location of a graphical user interface (GUI), at least one of the one or more confirmed chemical structures, and
- (ii) in a second designated location of the GUI, a portion of the electronic file, wherein the portion of the electronic file comprises the location of a confirmed chemical structure of the one or more confirmed chemical structures.

18. The computer-readable medium of claim 14, wherein the instructions, when executed, cause the processor to:
determine, based upon the one or more graphical features, that a first candidate chemical structure of the at least one candidate chemical structure lacks evidence of defined stereochemistry;
identify a bond center of the first candidate chemical structure;

analyze a plurality of sets of candidate bonds in relation to the first candidate chemical structure, wherein
each set of candidate bonds of the plurality of sets of candidate bonds is representative of a respective tetrahedral center, and
analyzing the plurality of sets of candidate bonds comprises identifying a matching stereo chemical configuration to the bond center of the first candidate chemical structure; and
assign, to the first candidate chemical structure, the matching stereo chemical configuration.

19. The computer-readable medium of claim 14, wherein a second filter of the one or more filters is configured to eliminate candidate chemical structures based at least in part on a determination that the given candidate chemical structure has a formula weight less than a minimum formula weight.

* * * * *